(12) United States Patent
Moir et al.

(10) Patent No.: US 8,690,812 B2
(45) Date of Patent: Apr. 8, 2014

(54) POST OPERATIVE KNEE BRACE WITH UNIFORM SYMMETRICAL LATERAL ADJUSTMENT

(75) Inventors: Russell S. Moir, Solvang, CA (US); Bryan K. Bowman, Roann, IN (US); Andrew M. Oplinger, Fort Wayne, IN (US); Robert A. Rosenberry, Solvang, CA (US)

(73) Assignee: United Surgical Associates, Inc., Solvang, CA (US)

( * ) Notice: Subject to any disclaimer, the term of this patent is extended or adjusted under 35 U.S.C. 154(b) by 147 days.

(21) Appl. No.: 13/344,547

(22) Filed: Jan. 5, 2012

(65) Prior Publication Data

US 2013/0178771 A1 Jul. 11, 2013

(51) Int. Cl.
*A61F 5/00* (2006.01)
*A43C 11/00* (2006.01)
(52) U.S. Cl.
USPC .............................................. 602/26; 24/68 R
(58) Field of Classification Search
USPC ............... 602/23, 5, 1, 26, 62, 63, 61, 60, 41; 24/68 R; 128/876; 2/338
See application file for complete search history.

(56) References Cited

U.S. PATENT DOCUMENTS

| | | | |
|---|---|---|---|
| 3,444,560 A | 5/1969 | Northup, Jr. | |
| 4,817,588 A | 4/1989 | Bledsoe | |
| 5,357,654 A | 10/1994 | Hsing-Chi | |
| 5,827,208 A | 10/1998 | Mason et al. | |
| 5,857,988 A | 1/1999 | Shirley | |
| 5,921,946 A | 7/1999 | Tillinghast et al. | |
| 5,950,245 A | 9/1999 | Binduga | |
| 6,290,664 B1 | 9/2001 | Nauert | |
| 6,413,232 B1 | 7/2002 | Townsend et al. | |
| 6,875,187 B2 | 4/2005 | Castillo | |
| 7,037,287 B2 | 5/2006 | Cormier et al. | |
| 7,059,329 B2 | 6/2006 | Mason et al. | |
| 7,074,201 B2 | 7/2006 | Reinecke et al. | |
| 7,117,569 B2 | 10/2006 | Bledsoe | |
| 7,198,610 B2 | 4/2007 | Ingimundarson et al. | |
| 7,201,728 B2 | 4/2007 | Sterling | |
| 7,235,059 B2 | 6/2007 | Mason et al. | |
| 7,311,687 B2 | 12/2007 | Hoffmeier et al. | |
| 7,431,708 B2 | 10/2008 | Sreeramagiri | |
| 7,485,103 B2 | 2/2009 | Mason et al. | |
| 7,597,675 B2 | 10/2009 | Ingimundarson et al. | |
| 7,757,303 B2 | 7/2010 | Miller | |
| 2009/0054819 A1 | 2/2009 | Einarsson | |
| 2009/0099495 A1* | 4/2009 | Campos et al. | 602/27 |
| 2009/0099562 A1 | 4/2009 | Ingimudarson et al. | |

(Continued)

*Primary Examiner* — Patricia Bianco
*Assistant Examiner* — Tarla Patel
(74) *Attorney, Agent, or Firm* — Felix L. Fischer

(57) ABSTRACT

A knee brace incorporates an upper attachment assembly received anteriorly on a thigh of and a lower attachment assembly to be received on a lower leg of a patent. Medial and lateral longitudinal supports are interconnected at medial and lateral hinges. An outer lateral arcuate support plate is attached to a first end of the lateral longitudinal support and an outer medial arcuate support plate is attached to a first end of the medial longitudinal support. Symmetrical lateral adjustment is accomplished with an anterior arcuate support plate and a lateral adjustment ratchet mounted to the anterior support plate. A lateral adjustment strap extends from the lateral arcuate support plate through the lateral adjustment ratchet. A lateral adjustment strap extends from the medial arcuate support plate through the lateral adjustment ratchet and rotation of the lateral adjustment ratchet symmetrically expands or retracts the lateral adjustment straps.

12 Claims, 15 Drawing Sheets

(56) References Cited

U.S. PATENT DOCUMENTS

| | | |
|---|---|---|
| 2009/0240181 A1 | 9/2009 | Sreeramagiri et al. |
| 2009/0259154 A1 | 10/2009 | Nace |
| 2010/0010409 A1 | 1/2010 | Bejarano |
| 2010/0162539 A1* | 7/2010 | Rancon ................. 24/70 ST |

* cited by examiner

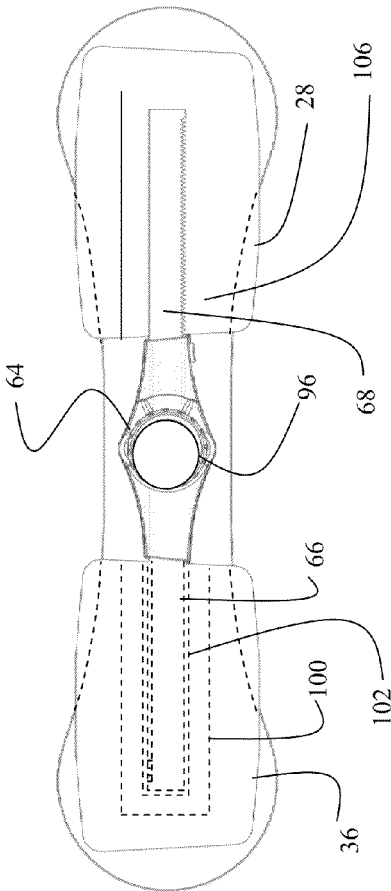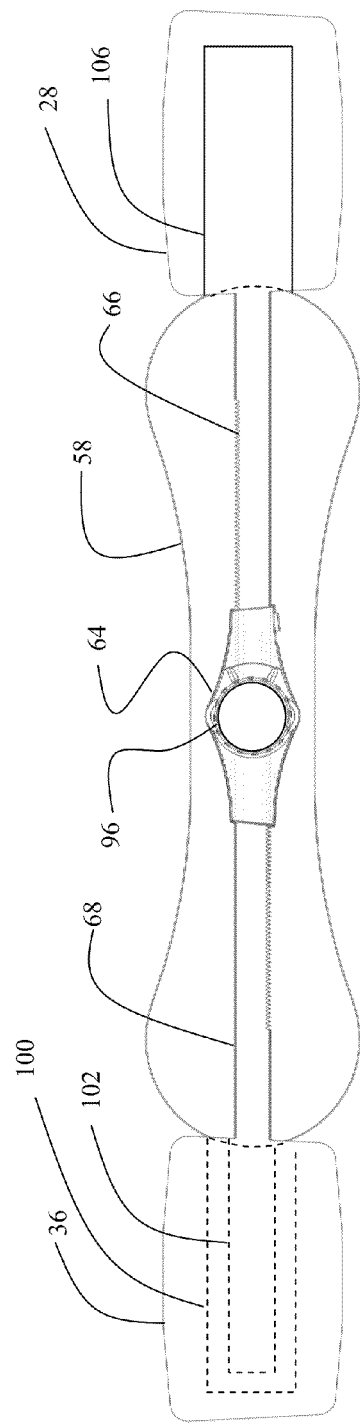

POST OPERATIVE KNEE BRACE WITH UNIFORM SYMMETRICAL LATERAL ADJUSTMENT

BACKGROUND INFORMATION

1. Field

Embodiments of the disclosure relate generally to the field of anatomical support braces and more particularly to a knee brace for post operative care with symmetrical lateral adjustment of brace size for anterior attachment.

2. Background

Surgery for repair of ligament or other injury to human knees is very common. For optimum post operative rehabilitation of the knee bracing to provide support for the healing knee while allowing nominal flexure of the knee is needed. Numerous bracing or support systems have been developed which are adapted specifically for supporting the knee while allowing bending for substantially normal walking motion. However, to properly adjust the support system to individual human legs with a wide variety of lateral, longitudinal and circumferential sizes while providing a secure attachment to avoid slippage is a challenge. Additionally, adjustment of the brace without undue manipulation of the patient's knee, which may be painful immediately after surgery, is often difficult.

It is therefore desirable to provide a post operative knee brace which can be anteriorly fitted and adjusted for lateral sizing with simplified symmetrical adjustment. It is further desirable that the post operative knee brace incorporate rapidly and easily adjustable tensioning for securing straps encircling the leg.

SUMMARY

Embodiments disclosed herein provide an attachment assembly for a post operative knee brace which employs lateral longitudinal support and a medial longitudinal support. An outer lateral arcuate support plate is attached to a first end of the lateral longitudinal support and an outer medial arcuate support plate is attached to a first end of the medial longitudinal support. A symmetrical lateral adjustment assembly incorporates an anterior arcuate support plate and a lateral adjustment ratchet mounted to the anterior support plate. A first lateral adjustment strap extends from the lateral arcuate support plate through the lateral adjustment ratchet. A second lateral adjustment strap extends from the medial arcuate support plate through the lateral adjustment ratchet and rotation of the lateral adjustment ratchet symmetrically expands or retracts the first and second lateral adjustment straps.

A post operative knee brace may incorporate an upper attachment assembly to be received anteriorly on a thigh of a patient and a lower attachment assembly to be received on a lower leg of a patent. The upper attachment assembly and lower attachment assembly each having a medial longitudinal support interconnected at a medial hinge and a lateral longitudinal support interconnected at a lateral hinge.

A tensioning assembly for the attachment assembly or other orthotic braces includes a securing element receiving a securing strap attached to a first arcuate support plate. The securing element has a ratchet strap. A tensioning ratchet is attached to a second arcuate support plate oppositely positioned from the first arcuate support plate for orthotic support. The tensioning ratchet receives the ratchet strap for tensioning the securing strap.

The features, functions, and advantages that have been discussed can be achieved independently in various embodiments of the present disclosure or may be combined in yet other embodiments further details of which can be seen with reference to the following description and drawings.

BRIEF DESCRIPTION OF THE DRAWINGS

FIG. 10 is a front flattened view of the lateral adjustment assembly in the fully retracted position with the anterior arcuate support plate removed for clarity;

FIG. 11 is a front flattened view of the lateral adjustment assembly in the fully extended position with the anterior arcuate support plate removed for clarity;

DETAILED DESCRIPTION

Figure 1:
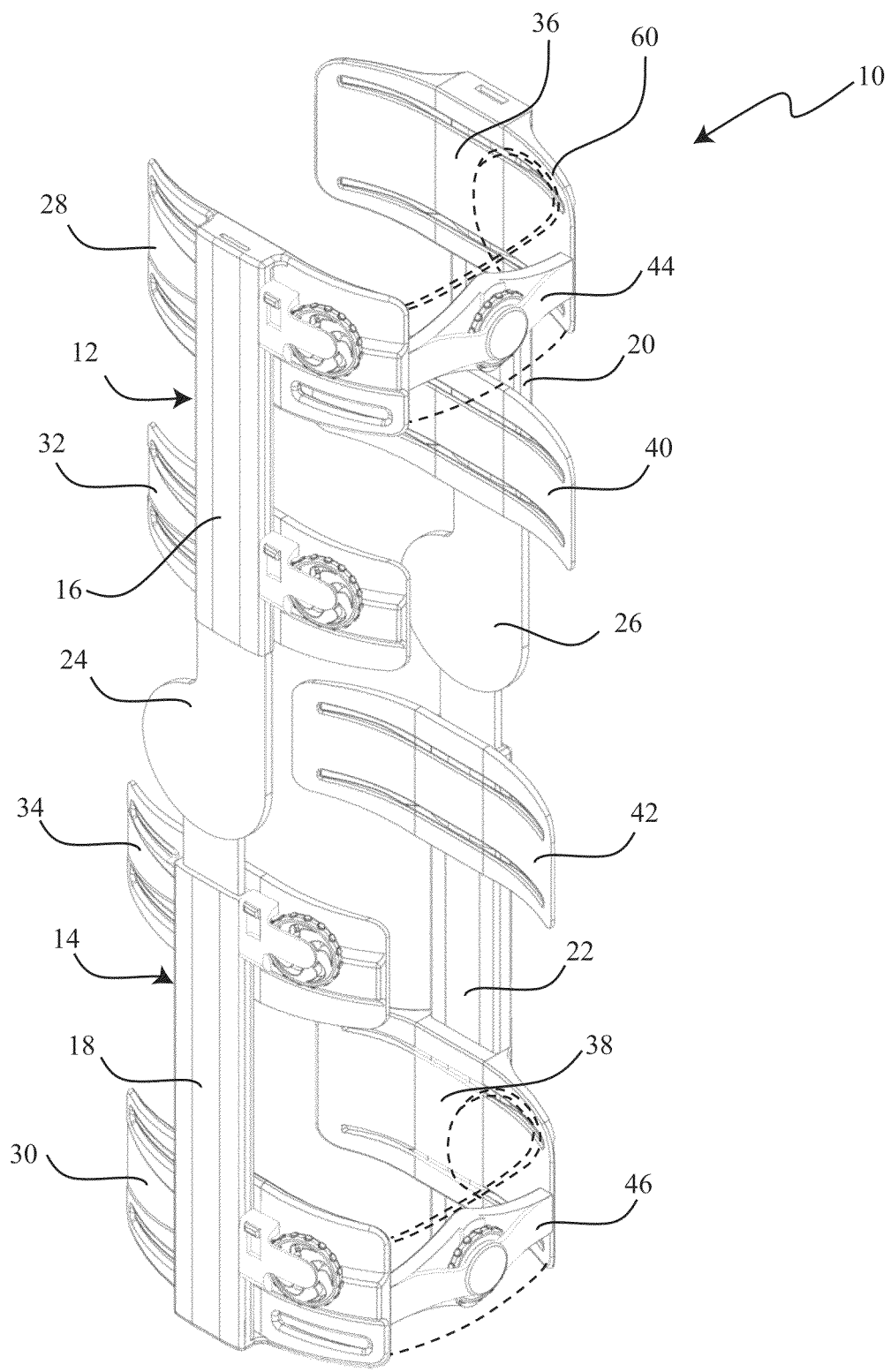
FIG. 1 is an isometric view of an embodiment of the post operative knee brace with uniform symmetrical lateral adjustment.

Embodiments disclosed herein provide a post operative knee brace with central anterior symmetrical lockable gear and pinion lateral adjustment of hinged longitudinal side bracing. Securing straps are tensioned with ratchet secured tension elements engaging fabric banding allowing the brace to support the leg against relative pivotal motion of the thigh and lower leg, extension or hyper-flexion while allowing bending of the knee. As shown in FIG. 1, a post operative knee brace 10 is composed of an upper attachment assembly 12 to be received on the thigh of the patient and a mirroring lower attachment assembly 14 to be received on the lower leg of the patient. Each attachment assembly (which is shown in detail in FIG. 2 for the upper attachment assembly) incorporates a lateral longitudinal support 16, 18 and a medial longitudinal support 20, 22. Hinges 24 and 26 interconnect the lateral and medial longitudinal supports, respectively, of the upper and lower attachment assemblies.

An outer lateral arcuate engagement plate 28, 30 and an inner lateral arcuate engagement plate 32, 34 are attached to the lateral longitudinal supports 16, 18 of the upper and lower attachment assemblies. An outer medial arcuate engagement plate 36, 38 and an inner medial arcuate engagement plate 40, 42 are attached to the medial longitudinal supports 20, 22 of the upper and lower attachment assemblies. The engagement plates are received against the medial and lateral portions of the thigh and lower leg of the patient to provide a distributed bearing area for the knee brace to support the leg with the hinges placed adjacent the knee.

A lateral adjustment assembly 44, 46 is attached between the outer lateral arcuate engagement plates 28, 30 and medial arcuate engagement plates 36, 38 for single point symmetrical adjustment of the lateral longitudinal supports 16, 18 and medial longitudinal supports 20, 22 for width and anterior/posterior depth on the thigh and lower leg, respectively.

Each arcuate engagement plate has an associated securing strap 48, 49 (shown in phantom in FIG. 2) as will be described in greater detail subsequently. Each securing strap 48 is received through a slot 50 in a securing element 52. The securing element 52 has an extending ratchet strap 54 which is received in a tension adjustment ratchet 56.

Figure 2:
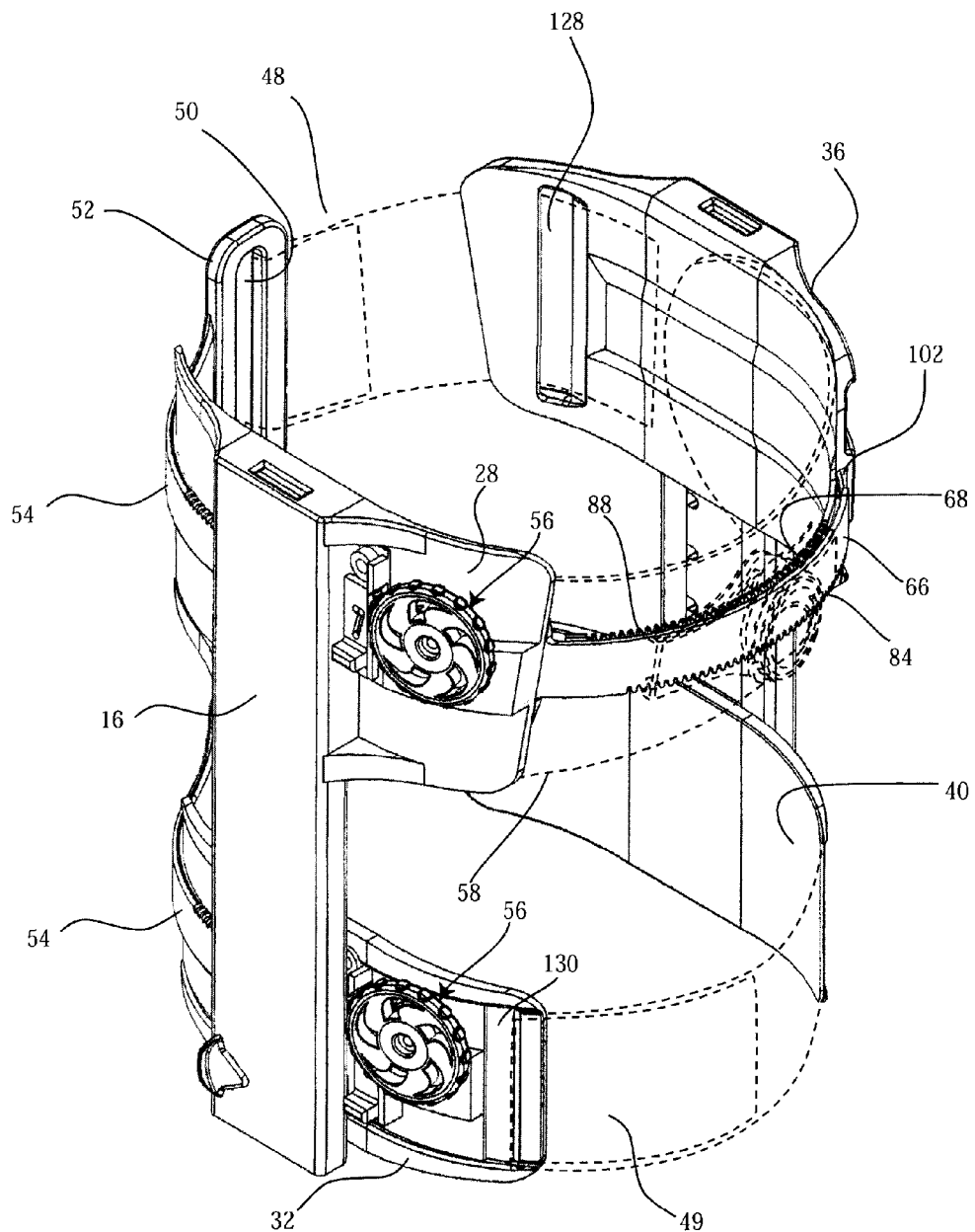
FIG. 2 is an isometric view of the upper attachment assembly of the knee brace.
Figure 3:
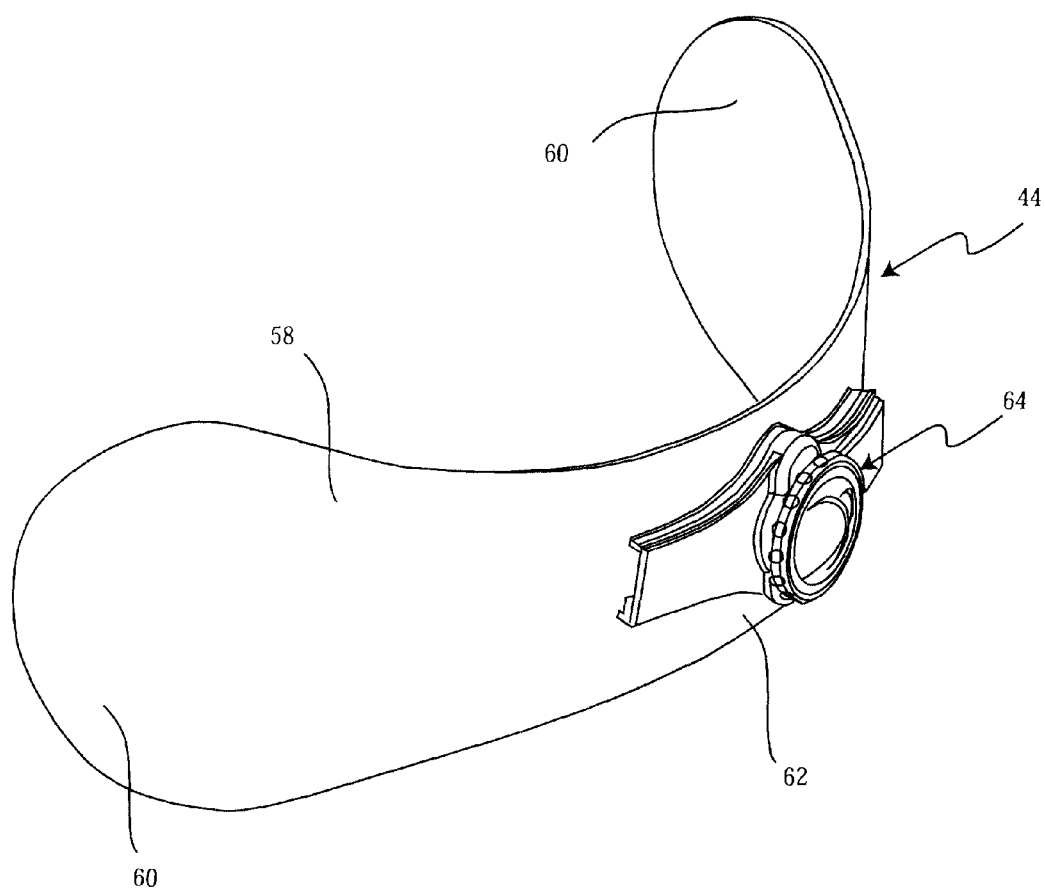
FIG. 3 is an isometric view of the lateral adjustment assembly.
Figure 4:
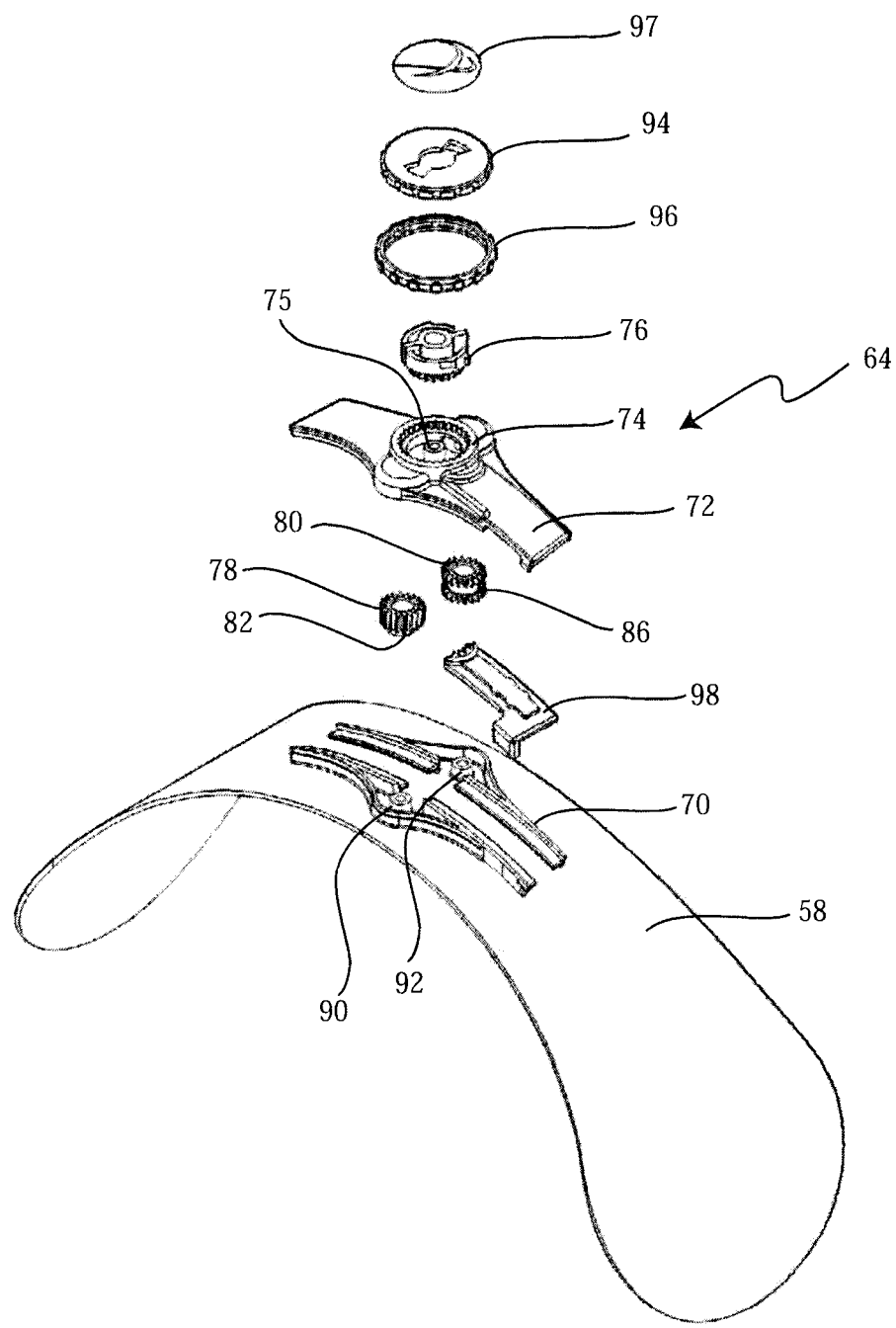
FIG. 4 is an exploded isometric view of the lateral adjustment assembly of FIG. 3.

The lateral adjustment assembly, detailed separately for upper adjustment assembly 44 in FIG. 3, has an anterior arcuate support plate 58 received across the anterior of the thigh of the patient (or the anterior of the lower leg for lateral adjustment assembly 46 of FIG. 1). Ears 60 are engaged between the leg and an inner surface of the lateral and medial arcuate engagement plates and extend into an anterior web 62 which supports a lateral adjustment ratchet 64. Overlapping lateral adjustment straps 66, 68 (shown in FIG. 2) which oppositely extend from the outer lateral and medial arcuate engagement plates 28, 36 extend through the lateral adjustment ratchet 64. An exploded view of the lateral adjustment assembly in FIG. 4 shows an inner support track 70 which receives and guides inner lateral adjustment strap 68. A cover 72 constrains and guides outer lateral adjustment strap 66 and provides a receiving housing 74 with an axle 75 for a central gear 76 and opposing planetary gears 78, 80. Planetary gear 78 has an engaging gear 82 for a lower edge tooth rack 84 on outer lateral adjustment strap 66. Planetary gear 80 has an engaging gear 86 for upper edge tooth rack 88 on inner lateral adjustment strap. Diametric opposition of the planetary gears 78 and 80 on the center gear 76 results in opposite rotation thereby expanding or retracting the inner and outer lateral adjustment straps symmetrically. For the embodiment shown in FIG. 4 axles 90, 92 for the planetary gears extend from the anterior arcuate support plate 58 adjacent the inner support track 70. For the embodiment shown, a dial 94 and knurled grip 96 engage the central gear 76 and close the receiving housing. A decorative cap 97 may be attached to the dial. A slide lock 98 releasably engages the central gear to lock the central gear and lateral adjustment assembly after adjustment, as will be described subsequently.

Figure 5:
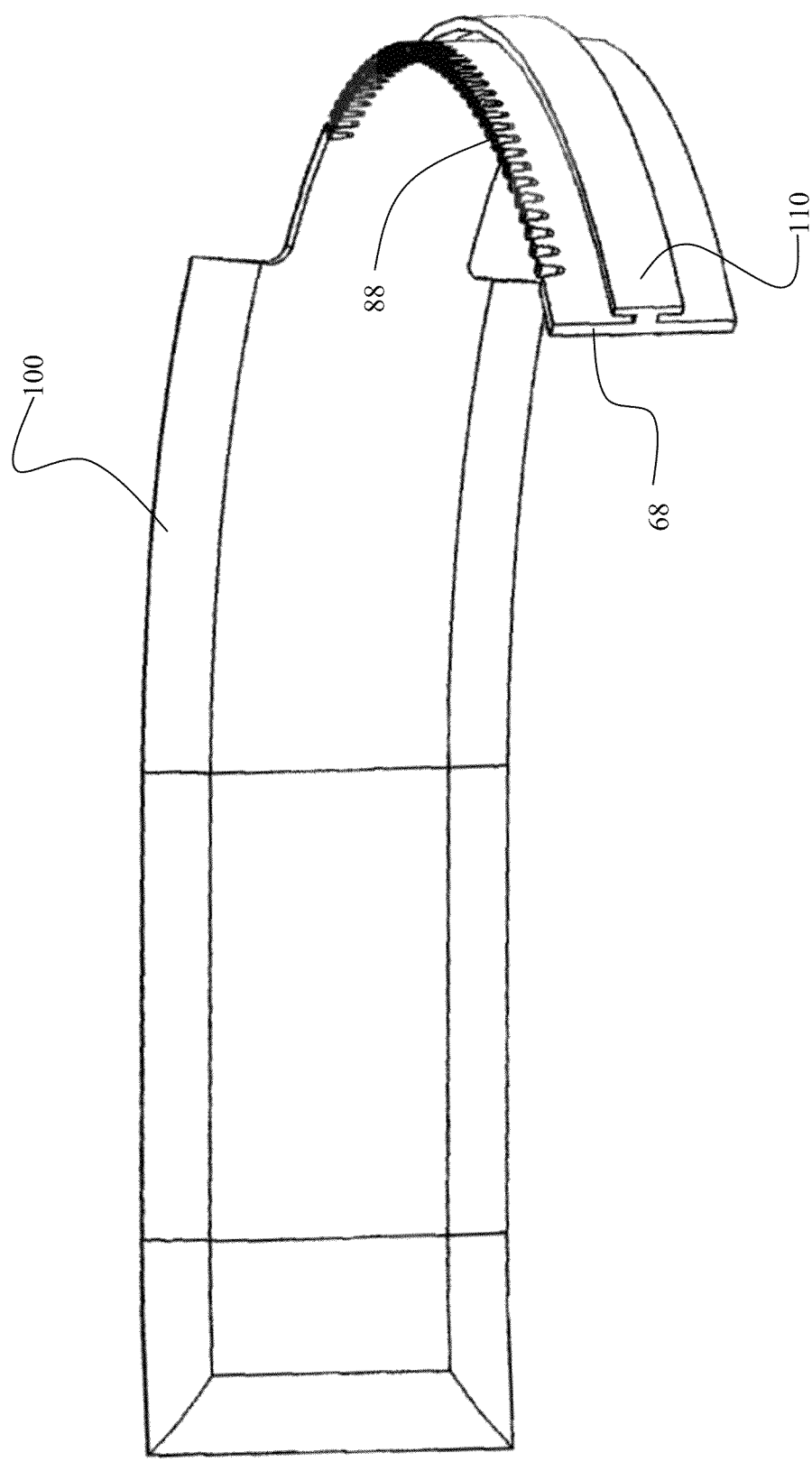
FIG. 5 is a detailed pictorial view of the inner lateral adjustment strap.
Figure 6:
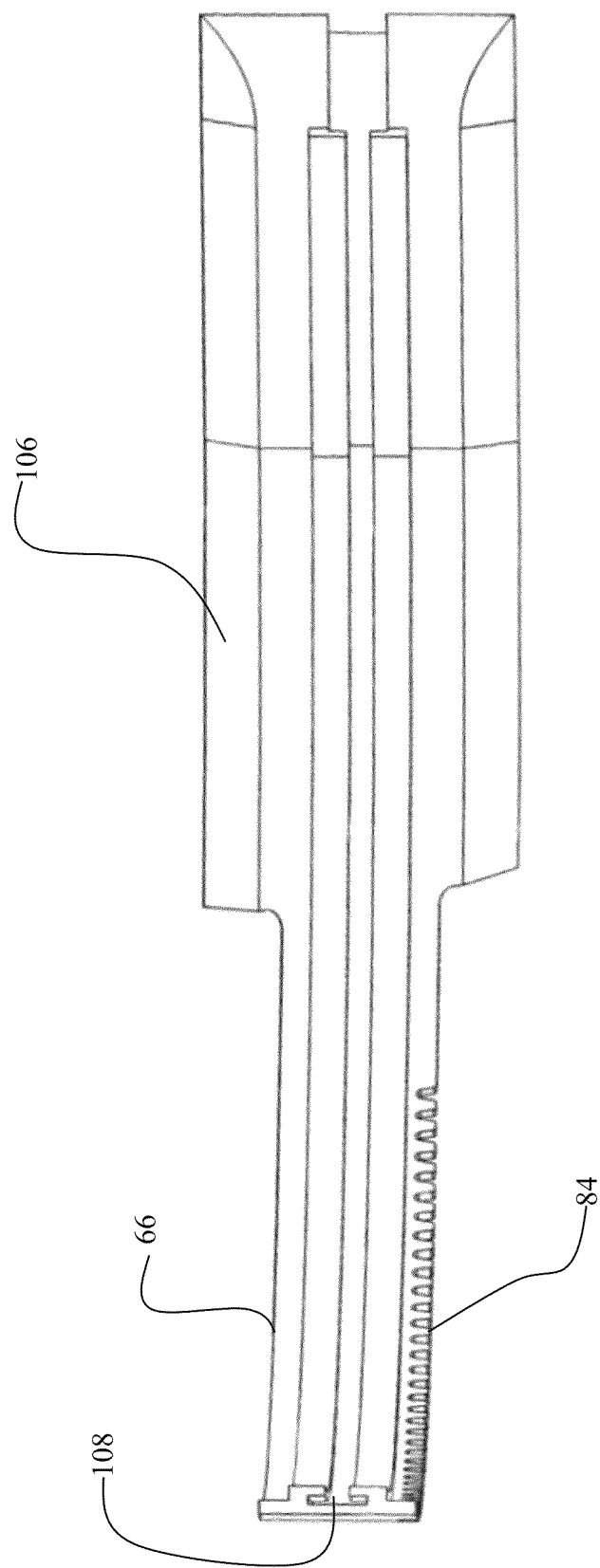
FIG. 6 is a detailed pictorial view of the outer lateral adjustment strap.
Figure 7:
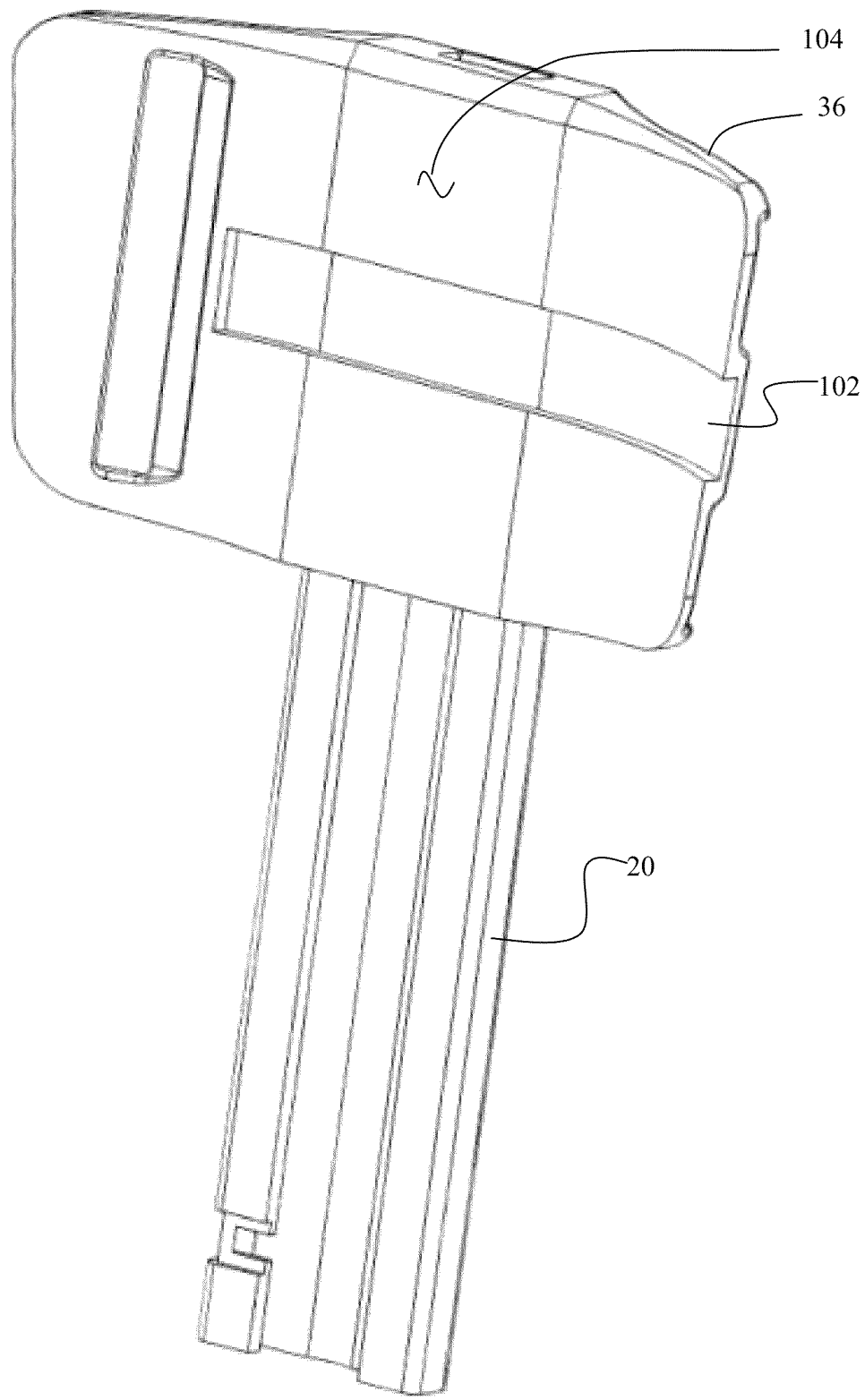
FIG. 7 is a detailed pictorial view of the outer medial arcuate engagement plate without the inner lateral adjustment strap attached.
Figure 8:
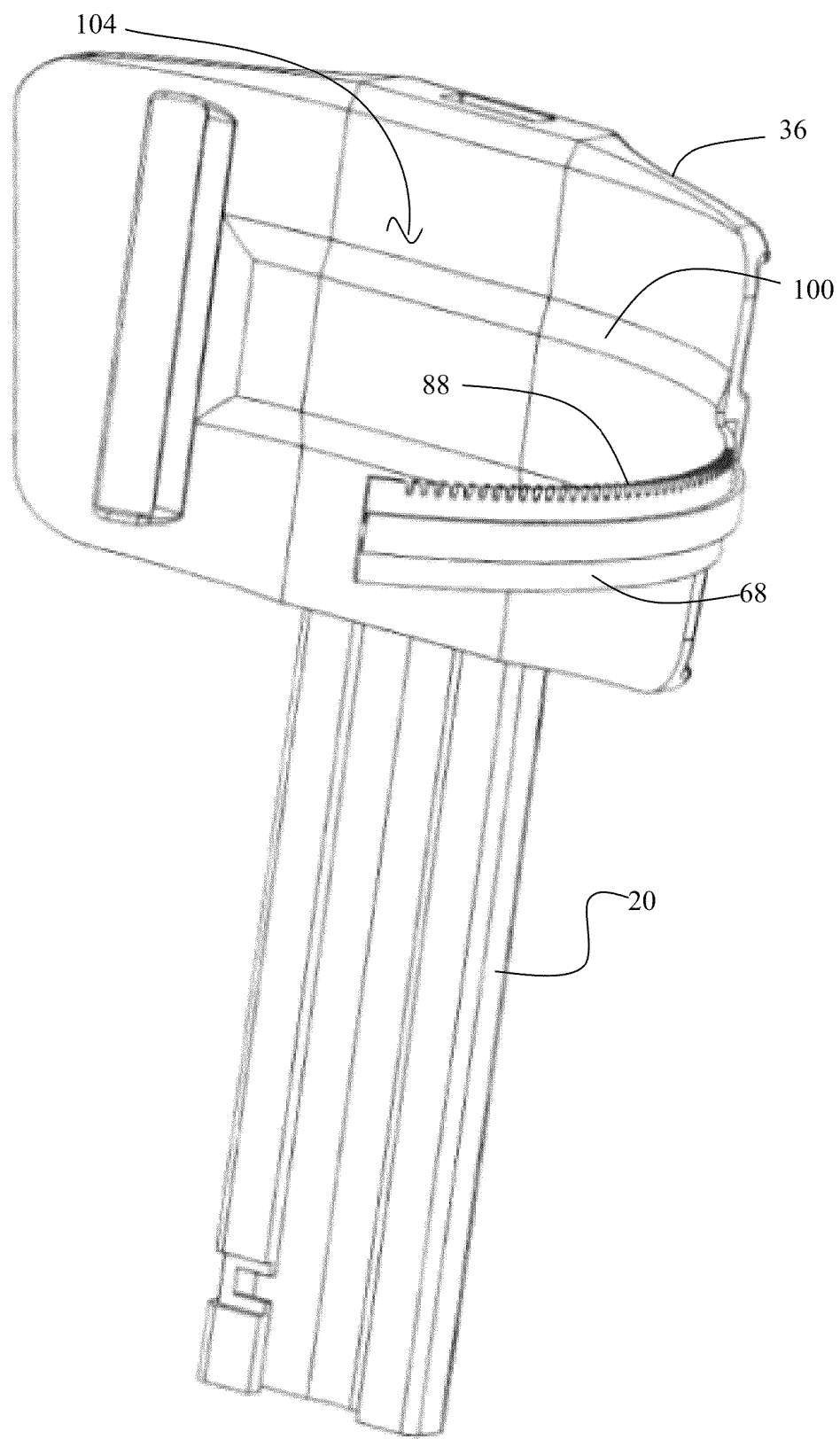
FIG. 8 is a detailed pictorial view of the outer medial arcuate engagement plate with the inner lateral adjustment strap attached.

Details of the inner lateral adjustment strap 68 and outer lateral adjustment strap 66 are shown in FIGS. 5 and 6. The inner lateral adjustment strap 68 is attached to the outer medial arcuate engagement plate 36 with an attachment tab 100 which extends peripherally from the strap width for adhesive or thermal weld attachment. In alternative embodiments, the attachment tab 100 may be secured by rivets or other mechanical fastening means. Similarly, the outer lateral adjustment strap 66 is attached to the outer lateral arcuate engagement plate 28 with an attachment tab 106. As shown in FIG. 7, the outer medial arcuate engagement plate 36 incorporates a relief 102 which receives the outer lateral adjustment strap 66 when retracted. Attachment tab 100 is received over the relief 102 as a cover and is secured to inner surface 104 of the outer medial arcuate engagement plate as shown in FIG. 8. The outer lateral adjustment strap 66 similarly incorporates an attachment tab 106 for attachment to outer lateral arcuate engagement plate 28.

Figure 9:
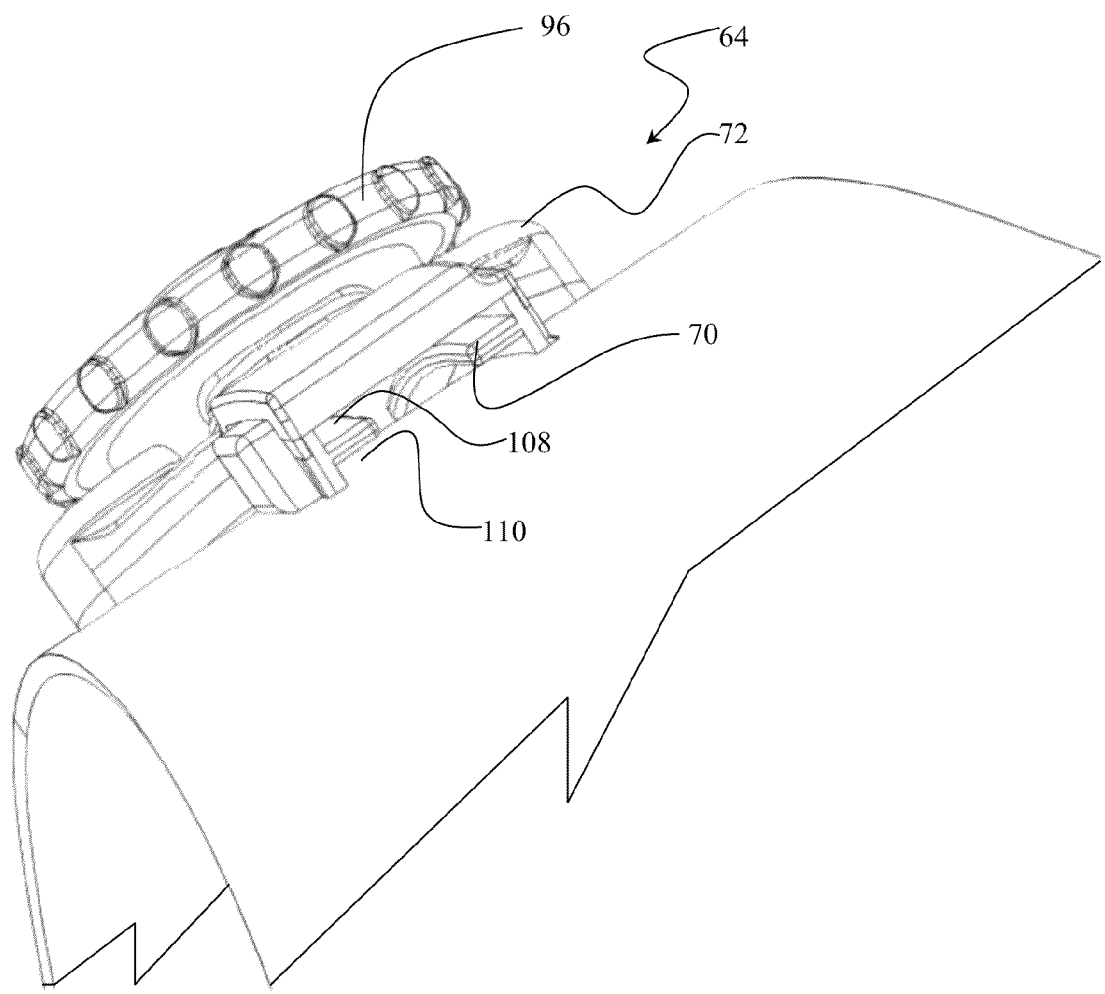
FIG. 9 is a detailed pictorial view of the inner support track and cover of the lateral adjustment assembly.

Returning to FIGS. 5 and 6, to maintain circumferential contact between the inner lateral adjustment strap 68 and outer lateral adjustment strap 66 when expanded and withdrawn from the reliefs in the arcuate engagement plates, outer lateral adjustment strap 66 incorporates a T-slot 108 which receives a mating T-extrusion 110 on inner lateral adjustment strap 68. The T-slot 108 extends on the attachment tab 106 to receive the inner lateral adjustment strap 68 in the retracted position. As shown in FIG. 9, the inner support track 70 is split to receive the joined T-extrusion and T-slot of the inner and outer lateral adjustment straps. The outer lateral engagement strap is received in volume 108 between the support track 70 and cover 72 and the inner lateral engagement strap is received in volume 110 between the support track and the web 62 of anterior arcuate support plate 58 to which the support track is attached. The adjustment straps are constrained by the web, track and cover for engagement by the engaging gears 82 and 86.

The outer lateral adjustment strap 66 and inner lateral adjustment strap 68 form a flexible arc on which the relative spacing of the medial and lateral arcuate support plates in each adjustment assembly can be adjusted.

As shown in FIG. 10, rotating the knurled grip 96 to turn the central gear 76 and, in turn, the planetary gears 78 and 80 (as described in FIG. 4) to retract the inner and outer lateral adjustment straps 68 and 66 places inner lateral adjustment strap 68 in the relief 102 in lateral arcuate support plate 28 as constrained by the attachment tab 100 of the outer lateral adjustment strap 66 and places outer lateral adjustment strap 66 in the relief 102 in medial arcuate support plate 36 as constrained by the attachment tab 106 previously described with respect to FIGS. 7 and 8. In this retracted position, lateral and medial arcuate support plates 28 and 36 are placed in closer proximity along the flexible arc created by the adjustment straps thereby symmetrically and simultaneously reducing the width and anterior/posterior depth of the lateral and medial arcuate support plates 28 and 36 as well as the attached longitudinal supports 16 and 20 (shown in FIG. 2) with respect to the leg of the patient.

As shown in FIG. 11, opposite rotation of the knurled grip 96 expands the inner and outer lateral adjustment straps, 68, 66 (withdrawing outer adjustment strap 66 from slot 102 in the medial arcuate support plates 36 and inner adjustment strap 68 with its T-extrusion from the T-slot in outer adjustment strap 66 as previously described) which places the support plates in further spaced relation along the flexible arc created by the lateral adjustment straps thereby symmetrically and simultaneously increasing the width and anterior/posterior depth of the lateral and medial arcuate support plates 28 and 36 as well as the attached longitudinal supports 16 and 20 (shown in FIG. 2) with respect to the leg of the patient.

Figure 12:
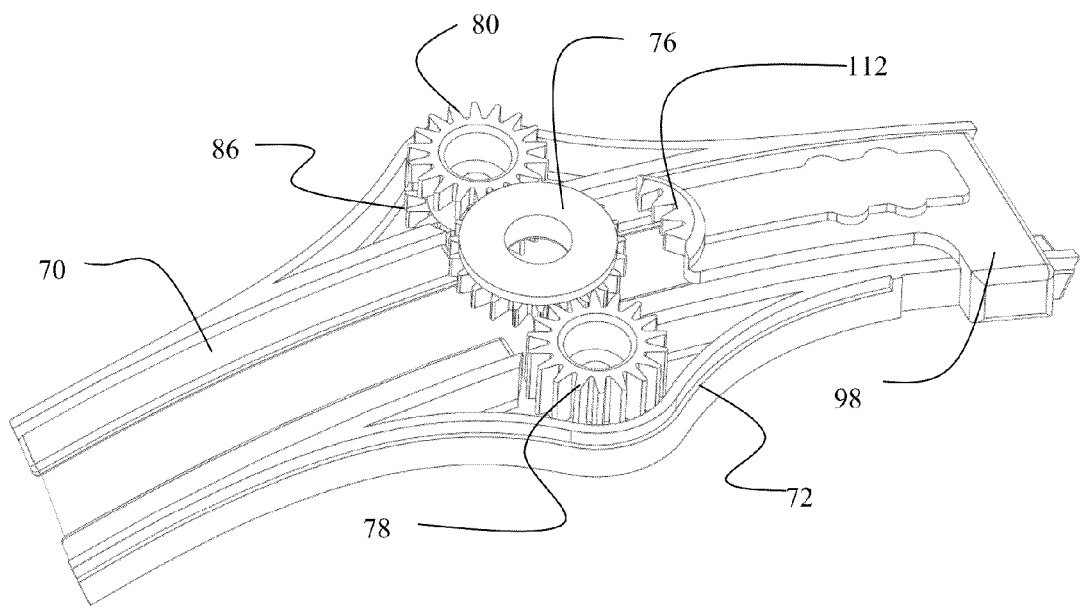
FIG. 12 is a detailed view of the lateral adjustment assembly with the cover removed to show the slide lock in the unengaged position.
Figure 13:
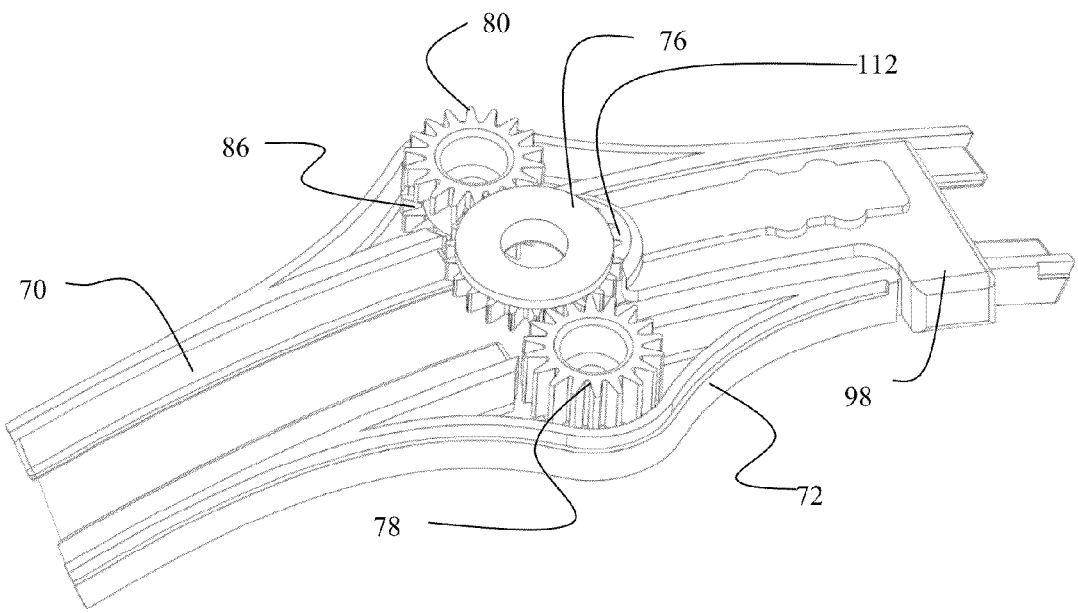
FIG. 13 is a detailed view of the lateral adjustment assembly with the cover removed to show the slide lock in the engaged position.

As shown in FIGS. 12 and 13, the gearing of the lateral adjustment ratchet 64 can be locked in place to secure the adjusted position with a slide lock 98. In FIG. 12, the slide lock 98 is withdrawn removing locking teeth 112 from contact with the central gear 76. This allows the central gear to be freely rotated by the knurled grip 96 (shown in FIGS. 3 and 4)

for rotation of the planetary gears 78 and 80 and associated engaging gears 82 and 86 for retraction or extension of the inner and outer lateral adjustment straps 68, 66 through engagement of the lower and upper tooth racks 84 and 88, respectively. When adjustment is complete, slide lock 98 is moved to engage locking teeth 112 with the central gear 76 thereby securing the adjusted position of the inner and outer lateral adjustment straps as shown in FIG. 13.

Figure 14:
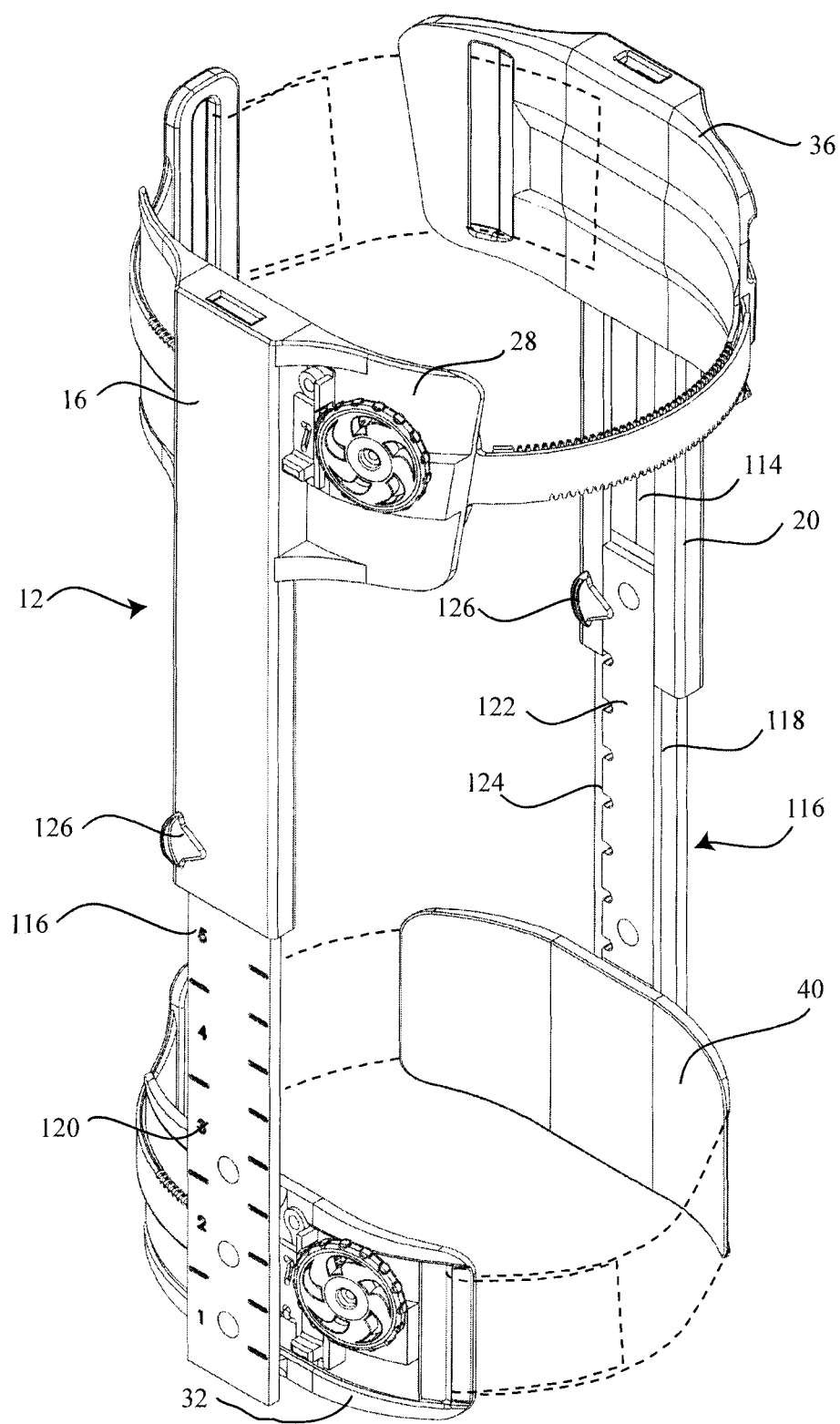
FIG. 14 is an isometric view of the lateral adjustment assembly with the longitudinal supports extended.

The upper and lower attachment assemblies 12 and 14 are also longitudinally adjustable to fit the length of the leg of a patient as shown in FIG. 14 for upper attachment assembly 12. Each longitudinal support 16, 20 incorporates a slot 114 which telescopically receives an extension member 116 with an upper end of the longitudinal support attached to an outer arcuate support plate and a lower end of the extension member attached to an inner arcuate extension plate. For the embodiment shown, the extension member 116 includes a tracking plate 118 that is closely received in the slot for lateral stability and incorporates on an outer face an indexing scale 120 for identifying extended length. A track bar 122 is attached to the tracking plate opposite the indexing scale 120. For the embodiment shown, slot 114 is partially open on the inner face to allow the track bar to protrude and engage the open sides of the slot providing further lateral stability. The track bar 122 incorporates indentations or cutouts 124 which correspond to selectable lengths on the indexing scale. A pull tab 126 releasably engages the cutouts 124 for locking telescoping adjustment of the extension member. Separate adjustment of the medial and lateral longitudinal members of both the upper and lower attachment assemblies allows custom fitting of the brace to the leg.

Figure 15:
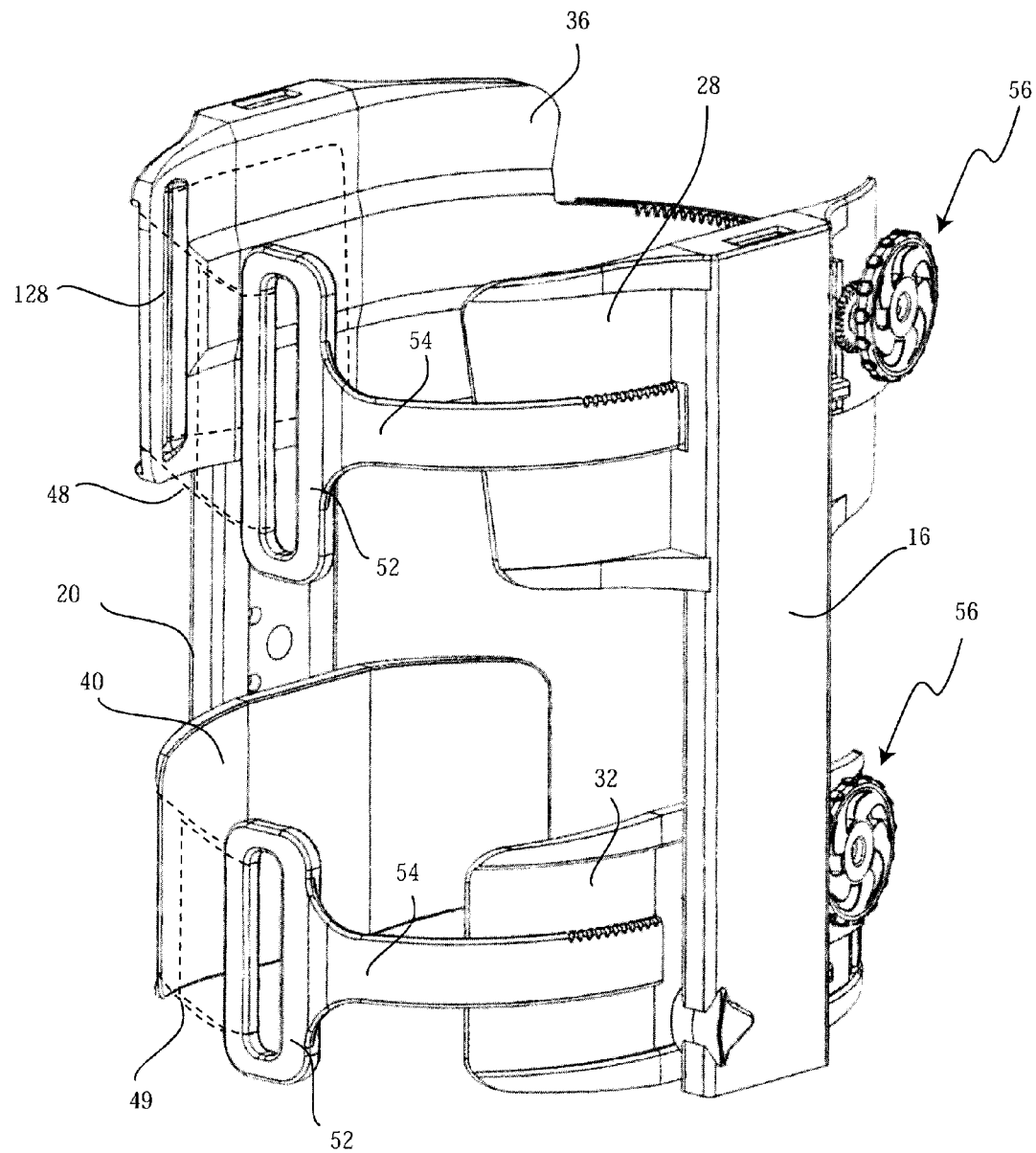
FIG. 15 is a detailed view of the lateral adjustment assembly showing the securing elements.

Once lateral and longitudinal adjustment of the brace is completed the securing elements 52 and associated tension adjustment ratchets 56 are employed to appropriately tension elastic or cloth bands (48 and 49 shown in phantom in FIG. 2) to affix the brace to the leg. This securing system may be employed on other orthotic devices as well. As shown in FIG. 15, each securing element incorporates a slot 50 to receive a loop of the cloth securing strap which may be secured to itself using hook and loop fasteners or other means known in the art. For the outer medial arcuate support plate 36 an aperture 128 (also seen in FIG. 2) receives an opposite loop of the cloth securing strap 48 allowing the strap to extend behind the leg. For the embodiment shown, the inner securing strap 49 extends from the slot 50 in the securing element 52 around the inner medial arcuate support plate 40, across the front of the leg and has the opposite attachment loop received through a slotted aperture 130 in the anterior extremity of the inner lateral arcuate support plate 32 as seen in FIG. 2.

Figure 16:
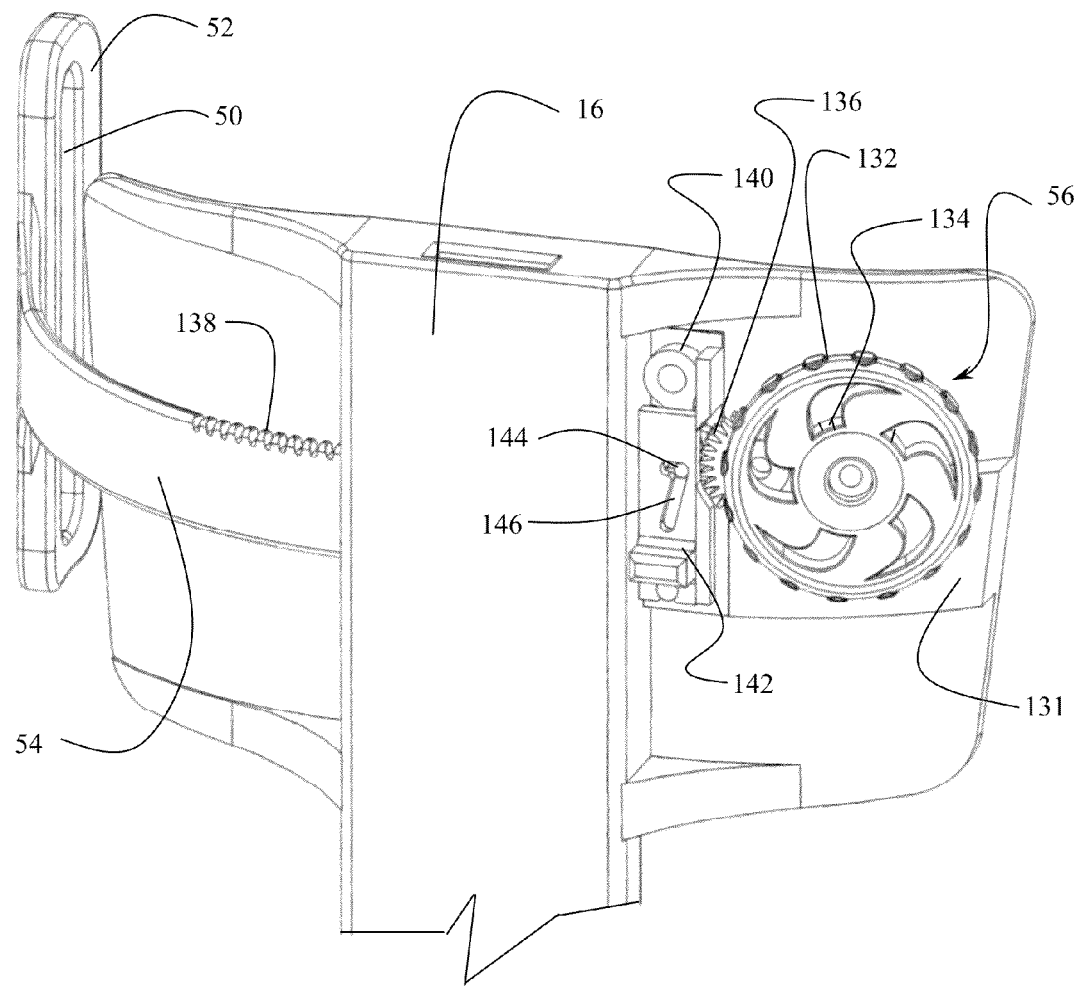
FIG. 16 is a detailed view of the tension adjustment ratchet for one securing element.

The securing straps may be roughly adjusted by positioning of the hook and loop fasteners when the brace is initially placed on the leg of the patient. When lateral and longitudinal adjustment are complete, tension adjustment ratchets 56, shown in detail in FIG. 16, are individually rotated to draw ratchet straps 54 on the securing elements through the ratchet assembly for tightening. The ratchet straps are received through slots in the longitudinal supports and reliefs or channels 131 in the lateral arcuate support plates to maintain alignment.

Figure 17:
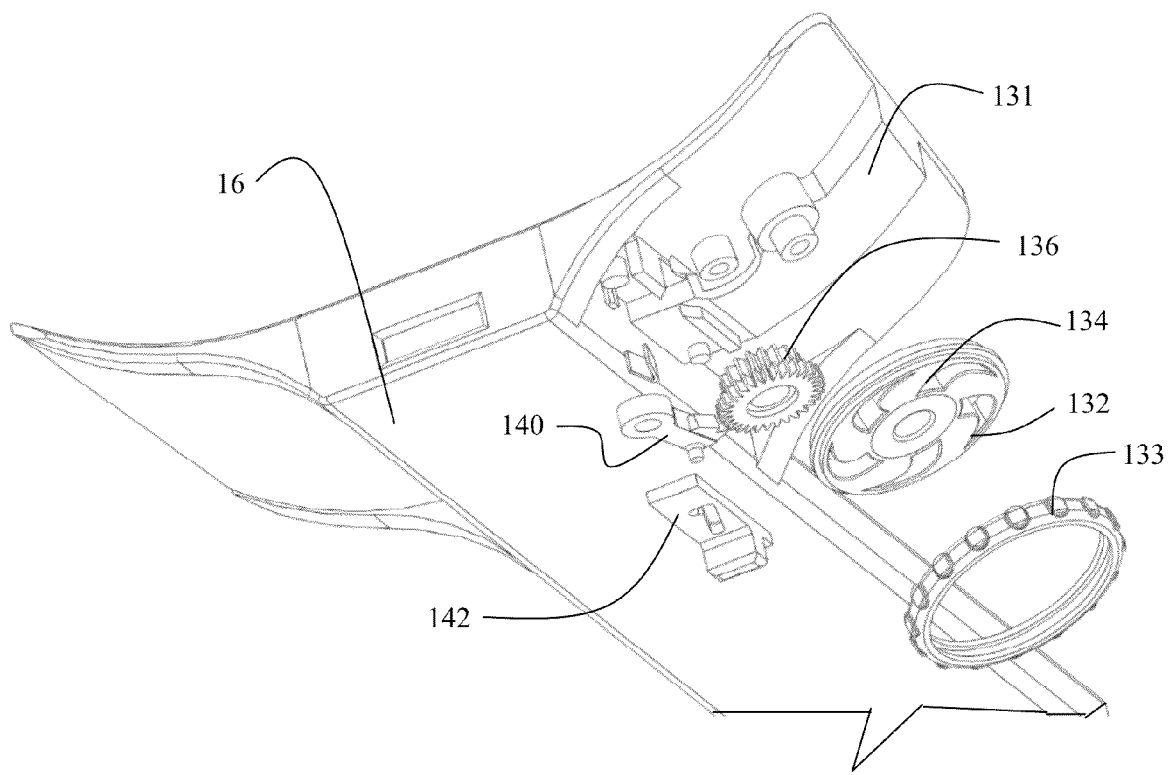
FIG. 17 is an exploded view of the tension adjustment ratchet.

The tension adjustment ratchets 56 employ a wheel 132 having a knurled rim 133 and a center gear 134 which engages a ratchet gear 136. The ratchet gear 136 engages a tooth rack 138 on the ratchet straps 54. A locking pawl 140 shown in detail in FIG. 17 engages the ratchet gear to fix tension. A pawl release 142 may be employed to release the pawl 140 from the ratchet gear 136 which will then free-wheel to allow tension on the securing elements to be released. A pin 144 on the locking pawl 140 is received in an angled slot 146 in the pawl release 142. Vertical translation of the pawl release urges the pin 144 in the slot to draw a pawl catch 146 away from the ratchet gear 136. When not in the released position, the pawl catch 146 engages the ratchet gear 136 for ratcheting operation.

In operation, the post operative knee brace is placed on the leg of a patient from an anterior aspect. This allows the patent to be lying or seated with the leg supported by a gurney. The anterior arcuate support plates 58 in the upper and lower adjustment assemblies 12, 14 are placed on the anterior thigh and anterior lower leg or shin of the patient. The securing straps 48, 49 in the upper and lower adjustment assembly may be loosely fitted around the thigh and calf respectively, looped through the slots 50 in the securing elements 52. The lateral adjustment ratchets 64 are then adjusted to symmetrically and simultaneously retract or expand the outer and inner lateral adjustment straps 66, 68 using the central gears 76 with associated planetary gears 78 and 80 to position the medial arcuate support plates and lateral arcuate support plates with the associated longitudinal supports for proper width and anterior/posterior positioning of the longitudinal supports. The lateral position is then fixed by engaging the slide locks 98. The longitudinal supports may then be adjusted for proper length with respect to the thigh and lower leg for optimal positioning of the hinges 24, 26 for bending support of the knee and separation of the inner and outer arcuate support plates for medial and lateral positioning on the leg for comfort and optimum securing location. The tension adjustment ratchets 56 at each lateral arcuate support plate are then rotated to tension the securing elements 52 to tighten the securing straps to properly secure the brace to the leg. While an example sequence is given, alternative sequences may be employed such as making all lateral and telescoping adjustments prior to fitting the securing straps. For removal, the pawl release 142 is employed to release ratchet gears 136 releasing the tension on the securing elements 52 and securing straps 48, 49.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. An attachment assembly for a post operative knee brace comprising:
    a lateral longitudinal support;
    a medial longitudinal support;
    an outer lateral arcuate support plate attached to a first end of the lateral longitudinal support;
    an outer medial arcuate support plate attached to a first end of the medial longitudinal support;
    a symmetrical lateral adjustment assembly having
        an anterior arcuate support plate;
        a lateral adjustment ratchet mounted to the anterior support plate;
        a first lateral adjustment strap extending from the lateral arcuate support plate through the lateral adjustment ratchet;
        a second lateral adjustment strap extending from the medial arcuate support plate through the lateral adjustment ratchet;
        wherein rotation of the lateral adjustment ratchet symmetrically expands or retracts the first and second lateral adjustment straps.

2. The attachment assembly for a post operative knee brace as defined in claim 1 further comprising
an inner lateral arcuate support plate attached to a second end of the lateral longitudinal support; and,
an inner medial arcuate support plate attached to a second end of the medial longitudinal support.

3. The attachment assembly for a post operative knee brace as defined in claim 2 further comprising:
a first securing element receiving a securing strap attached to the outer medial arcuate support plate, said securing element having a first ratchet strap;
a tensioning ratchet attached to the outer lateral arcuate support plate and receiving the first ratchet strap;
a second securing element receiving a securing strap attached to the inner medial arcuate support plate, said second securing element having a second ratchet strap; and,
a tensioning ratchet attached to the inner lateral arcuate support plate and receiving the second ratchet strap.

4. The attachment assembly for a post operative knee brace as defined in claim 1 wherein the first lateral adjustment strap incorporates a tooth rack in a first orientation engaged by a first planetary gear in the lateral adjustment ratchet and the second lateral adjustment strap incorporates a tooth rack in a second orientation opposite the first orientation and engaged by a second planetary gear in the lateral adjustment ratchet.

5. The attachment assembly for a post operative knee brace as defined in claim 1 further comprising:
a securing element receiving a securing strap attached to the outer medial arcuate support plate, said securing element having a ratchet strap; and,
a tensioning ratchet attached to the outer lateral arcuate support plate and receiving the ratchet strap.

6. A tensioning assembly for orthotic braces comprising:
a securing element receiving a securing strap attached to a first arcuate support plate, said securing element having a ratchet strap; and,
a tensioning ratchet attached to a second arcuate support plate oppositely positioned from the first arcuate support plate for orthotic support said tensioning ratchet receiving the ratchet strap;
a third arcuate support plate attached in relative relation to the first arcuate support plate for longitudinal support;
a fourth arcuate support plate attached in relative relation to the second arcuate support plate for longitudinal support;
a second securing element receiving a securing strap attached to the third arcuate support plate, said second securing element having a second ratchet strap; and,
a second tensioning ratchet attached to the fourth arcuate support plate and receiving the second ratchet strap.

7. A post operative knee brace comprising:
an upper attachment assembly to be received on a thigh of a patient;
a lower attachment assembly to be received on a lower leg of a patent, said upper attachment assembly and lower attachment assembly each having a medial longitudinal support interconnected at a medial hinge and a lateral longitudinal support interconnected at a lateral hinge;
each of said upper attachment assembly and lower attachment assembly having
an outer lateral arcuate support plate attached to a first end of the lateral longitudinal support;
an outer medial arcuate support plate attached to a first end of the medial longitudinal support;
a symmetrical lateral adjustment assembly having
an anterior arcuate support plate;
a lateral adjustment ratchet mounted to the anterior support plate;
a first lateral adjustment strap extending from the lateral arcuate support plate through the lateral adjustment ratchet;
a second lateral adjustment strap extending from the medial arcuate support plate through the lateral adjustment ratchet;
wherein rotation of the lateral adjustment ratchet symmetrically expands or retracts the first and second lateral adjustment straps.

8. The post operative knee brace as defined in claim 7 wherein each attachment assembly further comprises:
an inner lateral arcuate support plate attached to a second end of the lateral longitudinal support; and,
an inner medial arcuate support plate attached to a second end of the medial longitudinal support.

9. The post operative knee brace as defined in claim 8 wherein each attachment assembly further comprises:
a first securing element receiving a securing strap attached to the outer medial arcuate support plate, said securing element having a first ratchet strap;
a tensioning ratchet attached to the outer lateral arcuate support plate and receiving the first ratchet strap;
a second securing element receiving a securing strap attached to the inner medial arcuate support plate, said second securing element having a second ratchet strap; and,
a tensioning ratchet attached to the inner lateral arcuate support plate and receiving the second ratchet strap.

10. A method for adjustment of a post operative knee brace comprising:
placing a post operative knee brace on the leg of a patient from an anterior aspect with anterior arcuate support plates in an upper and a lower adjustment assemblies placed on the anterior thigh and anterior lower leg of the patient;
adjusting lateral adjustment ratchets to symmetrically retract or expand opposed lateral adjustment straps using central gears;
positioning medial arcuate support plates and lateral arcuate support plates with associated medial and lateral longitudinal supports for proper width and anterior/posterior positioning of the longitudinal supports; and,
fixing the lateral position by engaging slide locks.

11. The method of claim 10 further comprising adjusting the longitudinal supports for proper length with respect to the thigh and lower leg for optimal positioning of hinges for bending support of the knee and separation of the inner and outer arcuate support plates for medial and lateral positioning on the leg for comfort and optimum securing location.

12. The method of claim 10 further comprising
loosely fitting securing straps in the upper and lower adjustment assembly around the thigh and calf respectively;
looping the securing straps through slots in securing elements; and,
rotating tension adjustment ratchets at each lateral arcuate support plate to tension the securing elements to tighten the securing straps to properly secure the brace to the leg.

* * * * *